United States Patent [19]

Schindler et al.

[11] 4,265,249

[45] May 5, 1981

[54] CATHETER DEVICE AND SYSTEM FOR CONTINUOUS CHEMICAL ANALYSIS OF BODY FLUIDS IN VIVO

[75] Inventors: Johannes G. Schindler, Marburg, Lahn; Wilfried Schael, Bad Homburg, both of Fed. Rep. of Germany

[73] Assignee: Dr. E. Fresenius Chemisch pharmazeutisch Industrie KG, Bad Homburg, Fed. Rep. of Germany

[21] Appl. No.: 928,914

[22] Filed: Jul. 28, 1978

[30] Foreign Application Priority Data

Jul. 29, 1977 [DE] Fed. Rep. of Germany ....... 2734247

[51] Int. Cl.³ .............................................. A61B 5/00
[52] U.S. Cl. .................................. 128/635; 128/214 E; 128/349 R
[58] Field of Search ............ 128/213 A, 214.2, 214 B, 128/214 R, 348, 349 B, 349 R, 632, 673, 748, 635; 3/1; 210/321 B, 22, DIG. 23; 422/100, 101

[56] References Cited

U.S. PATENT DOCUMENTS

| | | | |
|---|---|---|---|
| 2,936,761 | 5/1960 | Snyder | 128/349 B |
| 3,489,647 | 1/1970 | Kolobow | 3/1X |
| 3,512,517 | 5/1970 | Kadish et al. | 128/214 R |
| 3,520,298 | 7/1970 | Lange | 128/240 X |
| 3,623,960 | 11/1971 | Williams | 128/635 X |
| 3,640,269 | 2/1972 | Delgado | 128/769 X |
| 3,658,053 | 4/1972 | Fergusson et al. | 128/632 |
| 3,981,299 | 9/1976 | Murray | 128/349 B |
| 4,094,775 | 6/1978 | Mueller | 210/321 B X |

FOREIGN PATENT DOCUMENTS 1280481 3/1960 France ................. 128/349 B

OTHER PUBLICATIONS

Boen et al., "Periodic Peritoneal Dialysis in the Management of Chronic Uremia, "*Trans. Amer. Soc. Artif., Inter. Orgs.*, vol. III, pp. 256–262, (1962).

*Primary Examiner*—Kyle L. Howell
*Attorney, Agent, or Firm*—Omri M. Behr; Martin Sachs

[57] ABSTRACT

A system for obtaining body fluids for continuous chemical analysis thereof includes a catheter for obtaining the material to be measured. The surface of the catheter is partially coated with a semi-permeable filter membrane. From the rear side of the filter membrane a plurality of channels are provided which communicate with a series of internal ducts which provide a fluid flow path for the material to be analyzed. The ducts are operatively coupled to a suction device pump and analyzing apparatus which are located remote from the catheter.

8 Claims, 3 Drawing Figures

CATHETER DEVICE AND SYSTEM FOR CONTINUOUS CHEMICAL ANALYSIS OF BODY FLUIDS

BACKGROUND OF THE INVENTION

1. Field of the Invention

The present invention relates to catheter devices and systems for continuous chemical analysis of body fluids, and in particular, relates to a catheter which may be inserted into the fluid carrying members of a living being for long periods of time to provide a continuous fluid flow for analysis.

2. Description of the Prior Art

The analysis of body fluids is of great importance in medical diagnostics. Up until the present time it was necessary to obtain samples of the body fluids such as, for example, blood, urine, gastric juices, etc., which were prepared and analyzed for their content of certain substances. This technique has the disadvantage of being discontinuous so that the results of the analysis only represented an instantaneous recording at the moment when the samples were taken. Where rapid changes in the samples were occurring, with the passing of time, many samples were required to be taken and analyzed at frequent intervals. This required large amounts of manual labor and placed an unnecessary strain on the patient.

For these and other reasons it has been a goal of the medical profession to devise a method to provide a continuous measurement technique. This technique requires the removal of the relevant fluids from the body with the aid of a catheter, analyzing it and subsequently returning it into the body. Returning the the fluid back into the body, of course, is only possible under certain conditions; for example, blood must be heparinized in order to prevent coagulation. Other body fluids may be influenced by the analysis so they may not be suitable for returning into the body without taking certain precautions. In some cases it may be possible to utilize a substitute or replacement fluid to replace that which was taken out of the body.

Since macromolecular (high molecular weight) and corpuscular components of the body fluid often interfere with the analysis, the latter must be removed before measurement. For this purpose, dialysis and ultrafiltration have proved to be successful. These techniques have been described by O. Aziz and R. Dennhardt in an article entitled Ultrafiltration of Circulating Blood in Vivo. Pflugers Archive, Volume 341 (1973), page 347; and by D. Sailer, G. Berg and F. Matzkies in an article entitled Zur kontinuierlichen Glukosevestimnung in Vivo. Biomed. Technik, Volume 19 (1974), page 134.

Nevertheless, the continuous removal of blood and other body fluids represents a large burden for the patient.

SUMMARY OF THE INVENTION

The present invention overcomes the shortcomings of the prior art by using a filter catheter for taking samples. The filter catheter makes ultrafiltration or dialysis of the ions and of the low molecular weight components of the body fluid directly in the living body. If only the low molecular weight components are removed from the body and foreign body substances do not reach the body fluid in any way, the patient is not placed under any significant strain. A plurality of measurement centers can be used. These measurement centers will not be spoiled or damaged by the material to be measured and contamination of the liquid under investigation will not take place if the present technique is utilized.

A system for obtaining body fluids for continuous chemical analysis thereof, according to the principles of the present invention comprises, in combination, a catheter adapted to be inserted into the fluid carrying members of a living body for obtaining continuous sampling. The catheter includes a body portion having at least three ducts therein, each provides a fluid flow path to the surface of the body portion. A semi-permeable membrane circumscribes part of the body portion and functions as a filter which is permeable to the substances to be analyzed and impermeable to high molecular weight and corpuscular portions of the fluid. A suction device is provided for guiding away the filtrate of the inside of the filter membrane in one of the ducts. External means are provided for continually analyzing the fluid obtained by the suction device. A rinsing device supplies liquid to a second duct and a third duct is provided for supplying medicaments thereto into the body.

BRIEF DESCRIPTION OF THE DRAWINGS

In order that the invention may be more fully understood, it will now be described, by way of example, with reference to the accompanying drawing in which.

DESCRIPTION OF THE PREFERRED EMBODIMENTS

Figure 1:
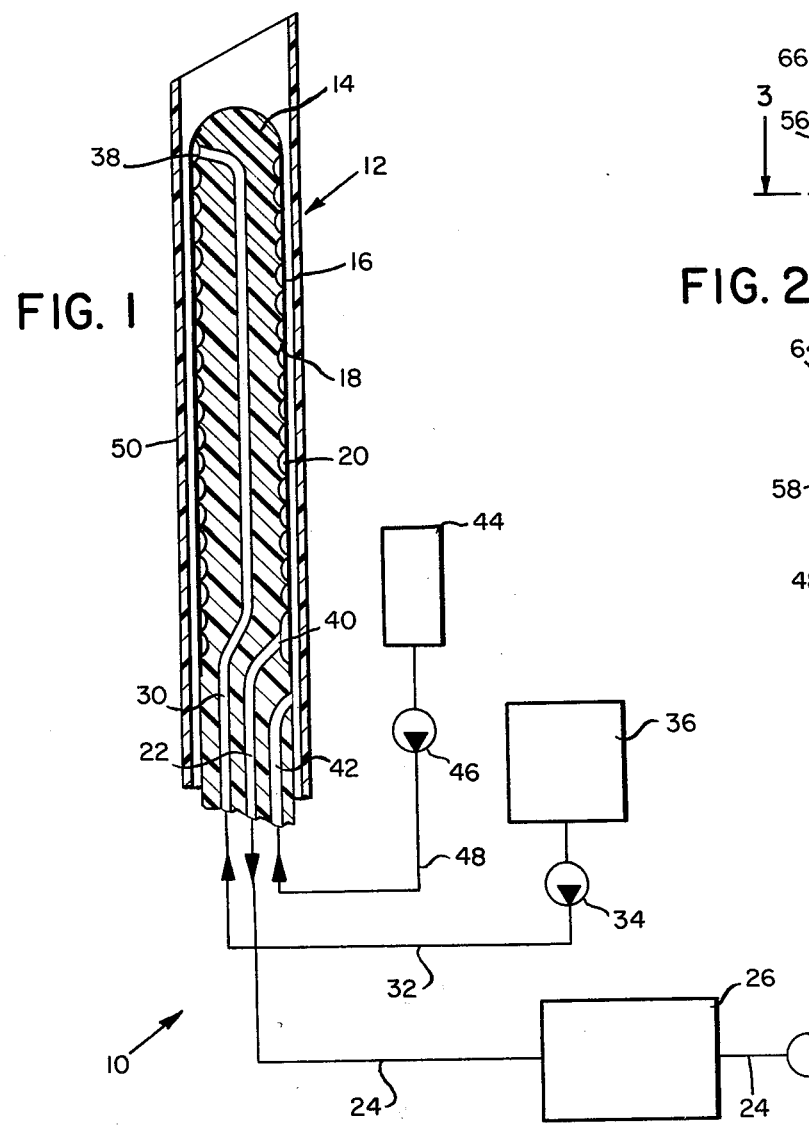
FIG. 1 is a pictorial representation of the system, according to the principles of the present invention, showing the catheter in cross-section with the components utilized in conjunction therewith.

Referring now to the figures, and in particular to FIG. 1, there is shown a system 10 for obtaining body fluids by continuous chemical analysis thereof. The system 10 includes a catheter 12 which has a body portion 14 fabricated preferably from a solid but flexible material such as plastic and has a length of approximately 350 millimeters (mm), for example, as well as, a diameter of approximately 4 millimeters (mm). The body portion 14 is provided with a conventional type of connection having provisions for the supply and removal of fluids.

The body portion 14 of the catheter 12 is generally cylindrically-shaped and has the major portion of its surface area covered with a semi-permeable membrane 16 which is permeable to the substances to be analyzed and non-permeable (impermeable) to higher molecular weight and corpuscular portions of the relevant body fluid, for example, the blood, urine, gastric juices. The membrane 16 rests upon a support structure, for example, the ribs or walls 18 that are created when a spiral 20 is cut in the surface of the body portion 14. At least one duct 22 communicates with the spirally formed channel 20 and serves to guide away the filtered body fluid or filtrate, via tubing 24, to a continuously operating analysis device 26 which may have electrochemical measurement sensors such as ion selective electrodes. A suction pump 28 shown coupled to the output of the analyzing device 26 may be positioned at its input rather than its output as presently shown and provides sufficient suction to continuously draw the filtrate out of the duct 22.

In many cases, it is advantageous to provide a liquid for rinsing out the filtrate from the spiral channel 20 and duct 22. Therefore, a second duct 30 is provided in the body portion 14 of the catheter 12 through which a rinsing liquid is supplied. The rinsing liquid enters, via a line 32, under pressure supplied by a pump 34 which draws the rinsing liquid from a container 36. Preferably, the rinsing liquid enters the spiral channel 20, via duct 30, at the opposite end of the catheter from which the filtrate is withdrawn. As presently shown in FIG. 1, the duct 30 communicates with the spiral channel 20 at a juncture 38 which is near the top of the body portion 14 while the filtrate is withdrawn, via duct 22, at the juncture 40 where duct 22 communicates with spiral channel 20.

A third channel 42 is not covered by the filter membrane 16, communicates directly with the body fluid and may be used to remove samples of the body fluid or introduce medicaments thereto, for example, substances inhibiting coagulation such as heparin which prevents coagulation of the blood at the surface of the catheter body 14. An appropriate infusion solution may be supplied from a second supply container 44 under pressure supplied by a pump 46, via line 48, which is coupled to duct 42. If the pump 46 is used for the infusion of a solution then the amount of output out of suction pump 28 is adjusted so that its output rate is slightly greater than that being supplied by pump 46. Since the amount of body fluid passing through the membrane 16 by way of the suction pump 28 is relatively small, the tension is only slightly burdened by the continuous removal of liquid so that usually no replacement of the removed liquid is necessary.

In operation, the analyzer 26 may continuously evaluate and analyze the different components in the filtrate. Chemicals may also be introduced into the filtrate without fear of influencing the fluid flow in the body since the filtrate is already rejected by the body.

A sheath member 50 may be used in conjunction with the body portion 14 of the catheter 12 to insure that the fluid carrying members of a living body do not collapse around the body portion 14, thereby cutting off the fluid flow. Thus, the sheath member 50 may be inserted into the fluid carrying member preventing the walls thereof from collapsing. The sheath being cylindrically-shaped and hollow has an inner diameter which is greater than the maximum outer diameter of the body portion 14 and is adapted to receive the body portion 14 therein while still permitting body fluids to flow around the body portion 14.

It is to be noted that duct 22 and 30 provide a fluid flow path of the body fluid which includes the membrane 16. Duct 42 provides a fluid flow path for the body fluids which does not include the membrane 16.

The catheter 12 may remain in the body for a relatively long time after implantation without placing any additional strain on the patient.

Figure 2:
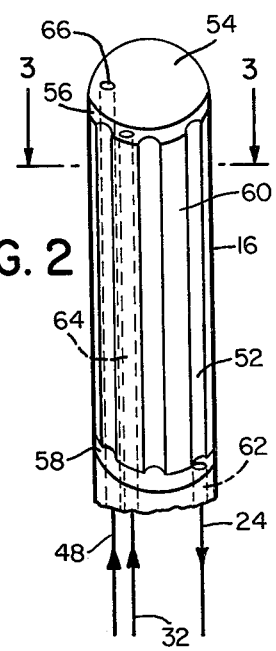
FIG. 2 is an isometric pictorial representation of an alternate embodiment of the body portion of the catheter with the filter membrane removed from the front surface thereof.

FIG. 2 shows an alternate embodiment of the present invention wherein the channels or grooves 52 generally are parallel to the longitudinal axis of the catheter body portion 54. A transverse set of grooves 56 and 58 are provided at either end of the body portion 54 in order to connect the longitudinal channels 52 and provide a continuous flow path there between. The membrane 16 covers the channels and rests tightly upon the ribs or walls 60 which remain after the grooves are provided in the body portion 54 and actually is the surface of the body portion. The external arrangement of lines 24, 32, and 48 are connected exactly as shown in the embodiment of FIG. 1. Duct 62 provides a fluid flow path to the body fluids which includes the membrane 16. Duct 64 provides a fluid flow path to the body fluids which also includes the membrane 16, while duct 66 provides a fluid flow path which communicates directly with the body fluids. The opening of duct 66, although shown at the top of body portion 54 in FIG. 2, may be located below groove 58, if desired. Although single openings have been shown for clarity where ducts 62 and 64 enter channels 56 and 58, it is understood that a plurality of such openings may be provided.

Figure 3:
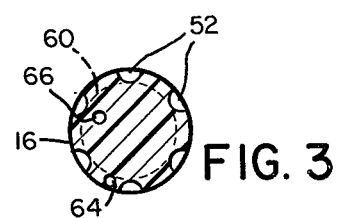
FIG. 3 is a cross-sectional view taken along the line 3—3 of FIG. 2.

FIG. 3 is a cross-sectional view taken along lines 3—3 of FIG. 2 to more clearly define the location of the grooves and channels provided in the body portion 54. Body portion 54 may also be used in combination with a sheath, not shown, to accomplish the same purpose as that explained heretofore.

Hereinbefore has been disclosed a catheter device and system for obtaining continuous flow of body fluids which may be continually analyzed. The components are relatively small and it is possible to construct the entire system to be portable with the analyzer being a microprocessing unit which may further control and react to the measured results obtained and feed medicaments such as, for example insulin, into the bloodstream in small amounts as required by the patient, thereby supplying modifications thereto as required.

It will be understood that various changes in the details, materials, arrangements of parts and operating conditions which have been herein described and illustrated in order to explain the nature of the invention may be made by those skilled in the art within the principles and scope of the present invention.

Having thus set forth the nature of the invention, what is claimed is:

1. A catheter for use with a system for obtaining body fluids from fluid carrying members for a continuous chemical analysis thereof comprising:
    (a) an elongated solid body portion having at least three ducts disposed therein, each said ducts being provided with an entrance at one end of said body portion and providing a fluid flow path to the surface of said body portion;
    (b) a semi-permeable membrane filter means circumscribing said body portion and supported thereby, leaving at least one of said ducts uncovered, said membrane being permeable to the substances to be analyzed and impermeable to high molecular weight and corpuscular portions of said fluids;
    (c) continuous channel means formed on the surface of said body portion for communicating with at least two of said ducts to provide a continuous fluid flow path, said membrane means covering said channels.

2. A catheter according to claim 1 wherein said continuous channel means forms a spiral on the surface of said body portion.

3. A catheter according to claim 1 wherein said continuous channel means includes a plurality of generally parallel paths.

4. A system for obtaining body fluids for a continuous chemical analysis thereof, comprising in combination:
    (a) catheter means adapted to be inserted into the fluid carrying members of a living being for obtaining continuous samples of said fluid, said catheter means including;
(i) an elongated body portion having at least three ducts therein each duct having an opening provided at one end of said body portion and providing a fluid flow path to the surface of said body portion, the surface of said body portion being provided with channels disposed about the circumference of said body portion, said channels providing a continuous fluid flow path with two of said ducts;
(ii) a semi-permeable membrane means circumscribing part of said body portion and supported thereby, leaving at least one of said ducts uncovered, said membrane being a filter and permeable to the substances to be analyzed and impermeable to high molecular weight and corpuscular portions of said fluid, said channels being disposed beneath said membrane;
(b) means for guiding away the filtrate from the inside of said filter membrane by providing a reduced pressure into one of said ducts;
(c) means for continually analyzing said fluids operatively coupled to said guiding away means;
(d) means coupled to said second duct for supplying a rinsing liquid thereto; and
(e) means coupled to said third duct for supplying medicaments thereto.

5. A system for obtaining body fluids for a continuous chemical analysis thereof, comprising in combination:
(a) catheter means adapted to be inserted into the fluid carrying members of a living being for obtaining continuous samples of said fluid, said catheter means including;
(i) an elongated body portion having at least three ducts therein each duct having an opening provided at one end of said body portion and providing a fluid flow path to the surface of said body portion,
(ii) a semi-permeable membrane means circumscribing part of said body portion and supported thereby, leaving at least one of said ducts uncovered, said membrane being a filter and permeable to the substances to be analyzed and impermeable to high molecular weight and corpuscular portions of said fluid;
(b) means for guiding away the filtrate from the inside of said filter membrane by providing a reduced pressure into one of said ducts;
(c) means for continually analyzing said fluid operatively coupled to said guiding away means;
(d) means coupled to said second duct for supplying a rinsing liquid thereto; and
(e) means coupled to said third duct for supplying medicaments thereto.

6. A system according to claim 5 wherein said body portion is provided with channels communicating with said ducts, said channels being disposed beneath said membrane and about the circumference of said body portion for permitting said filtrate and said rinsing liquids to flow therethrough in a continuous fluid flow path.

7. A system according to claim 6 wherein said channels form a spiral on the surface of said body portion.

8. A system according to claim 6 wherein said channels are generally parallel to the longitudinal axis of said body portion.

* * * * *